United States Patent [19]

Dart et al.

[11] Patent Number: 4,798,723

[45] Date of Patent: Jan. 17, 1989

[54] AGRICULTURAL PRODUCTS FROM *PSEUDOMONAS CEPACIA* STRAINS AND METHODS OF PREPARATION

[75] Inventors: Peter J. Dart, Fadden; K. Prakash Hebber, Canberra, both of Australia

[73] Assignee: Lubrizol Genetics, Inc., Wickliffe, Ohio

[21] Appl. No.: 106,986

[22] Filed: Oct. 5, 1987

Related U.S. Application Data

[63] Continuation of Ser. No. 891,212, Jul. 28, 1986, abandoned.

[51] Int. Cl.$^4$ ............................................. A01N 63/00
[52] U.S. Cl. ........................................ 424/93; 47/57.6; 435/243; 435/249; 435/253.3; 435/874
[58] Field of Search ................. 424/93; 435/243, 249, 435/253, 874; 47/57.6

[56] References Cited

U.S. PATENT DOCUMENTS 4,588,584 5/1986 Lumsden et al. ..................... 424/93

OTHER PUBLICATIONS

Kommedahl and Mew (1975) Phytopathology 65:296–300.
Kawamoto and Lorbeer (1976) Plant Dis. Reptr. 60:189–191.
R. D. Lumsden (1982) Phytopathology 72:709.
Cavileer and Peterson (1985) American Phytopathology Society Annual Meeting, p. 1344.
Elander et al. (1968) Applied Microbiol 16: 753–758.
Palleroni and Holmes (1981) Intl. J. System. Bacteriol. 31:479–481.
J. O. Becker (1984) "Isolation and Characterization of Antimycotic Bacteria from Rhizosphere Soil" in *Preceedings of British Crop Protection Conference (Pests and Diseases)*, vol. I, Nov. 19–22, 1984, BCPC Publications, Cryoden, U.K., pp. 365–370.
J. O. Becker et al. (1985) Med. Fac. Landbouww. Rijksuniv. Gent. 50/3b.

*Primary Examiner*—Howard E. Schain
*Attorney, Agent, or Firm*—Greenlee and Associates

[57] ABSTRACT

Agricultural methods of biological control and organisms useful in such methods are disclosed, such as a plant colonizing organisms and methods of biologically controlling plant disease caused by fungi. A novel type of *Pseudomonas cepacia* type Wisconsin has been identified. These strains and other *P. cepacia* strains described are useful as vectors for delivery to plants of beneficial products.

22 Claims, 6 Drawing Sheets

AGRICULTURAL PRODUCTS FROM *PSEUDOMONAS CEPACIA* STRAINS AND METHODS OF PREPARATION

This application is a continuation of application Ser. No. 891,212, filed July 28, 1986, now abandoned.

FIELD OF THE INVENTION

The present invention is directed to biological methods and products useful in agriculture. More specifically, the present invention is directed to a method of controlling plant fungal disease particularly those diseases caused by fungus of the genus Fusarium, certain biological control agents useful in such a method, and biological agents generally useful in agriculture.

BACKGROUND OF THE INVENTION

Fungi of the genus Fusarium are responsible for numerous crop plant diseases around the world. These fungi are particularly harmful to cereal crops, such as corn, sorghum and wheat. For example, one or more species of Fusarium can be isolated in every season from nearly every vegetative or reproductive part of corn in every corn-growing region of the United States. A particular species of Fusarium can occur singly or as part of a complex of Fusarium species or fungi of other genera. Depending upon weather, soil and the particular cereal variety, damage to the crop can range from negligible to extensive. A common occurrence, for example, is for a Fusarium infected cereal crop to be damaged if it comes under stress. The diseases caused by Fusarium fungi include seedling blight, root rot, stalk rot, and ear rot.

*Fusarium moniliforme* is the most widely prevalent and economically important Fusarium species found on corn in the United States, and is the most frequently isolated Fusarium species in shelled corn. Seed lots with 100% infection are not uncommon. It is also the most frequent cause of ear rot, and has been implicated in seedling blight and root rot. One of the primary diseases affecting the corn crop in the United States is stalk rot, and *F. moniliforme* is considered to be the predominant stalk rot fungus in at least 10 states: Florida, Idaho, Iowa, Minnesota, Nebraska, New Jersey, North Carolina, Pennsylvania, South Carolina, and Virginia. *F. moniliforme* is also known to produce a phytotoxin.

*Fusarium roseum* is found less often in corn kernels than *F. moniliforme*, primarily occurring in the humid sections of the corn belt eas of the Mississippi River and along the Atlantic seaboard. *F. roseum* is a cause of ear rot and seedling blight, and one of the important causes of stalk rot in the New England, Mid-Atlantic and Northern corn belt states. *F. roseum* also produces mycotoxins in kernels and stalks.

Additional species of Fusarium fungi which are of lesser importance than *F. moniliforme* and *F. roseum* in corn disease include *F. tricinctum*, *F. oxysporum*, and *F. soloni*. While these species are mainly of importance as parts of disease complexes, *F. tricinctum* has been reported to produce mycotoxins in kernels and stalks.

Fusarium fungi are not believed to be strong pathogens. Generally, they produce major symptoms and damage crops only when the crops are under stress. The advance of the fungi in the plant is determined largely by what stress is occurring and the rate of cell death in plant tissues. Fusarium fungi has a wide host range of cereals and grasses and very effective methods of survival in soil or plant residues. Wherever grasses or cereals are grown in the United States, a Fusarium infection of seedlings, roots, stalks, or ears is always possible. Thus, a method of controlling Fusarium infection in cereal crops is highly desirable. See generally, *Fusarium: Diseases, Biology and Taxonomy* (P. E. Nelson, T. A. Toussoun, and R. J. Cook eds. 1981); Christensen and Wilcoxson (1966) Amer. Phytopathol. Soc. Monogr. No. 3, 59 p.; Koehler (1959) Illinois Agric. Exp. Stn. Bull. 639. 87 p.; Koehler (1960) Illinois Agric. Exp. Stn. Bull. 658. 90 p.

Other plant pathogenic fungi which have significant impact include Pythium spp., Phytophthora spp., Sclerotinia spp., Sclerotium spp., Rhizoctonia spp., and Colletotrichum spp., Pythium spp. are the causive agents of a wide range of diseases on many crop plants, including damping off, hollow stem, stem rots, root rots and wilts. Important strains include, among others, *P. ultimun*, *P. debaryanum* and *P. aphanidermatum*. Phytophthora spp. are also associated with a variety of plant diseases including damping off, leaf blight, petiole and stem infection and root infections. Plant pathogenic strains include, among others, *Phytophthora porri*, *P. capsici*, *P. cryptogea*, *P. mexicana*, *P. cinnamomi* (root decay) and *P. infestans* (late blight in tomatoes). Sclerotinia spp., causative agents of white rot, are widely dispersed and have a wide host range. Important plant pathogens include *Sclerotinia sclerotiorum*, *S. minor* and *S. intermedia*. Sclerotium spp. and *S. rolfsii* in particular are associated with stem root rots and blights (Southern blight). These pathogens affect many crops including rice, peanut and sunflower. Rhizoctonia spp. (literally root killers) are associated with root rots. Rhizoctonia are the mycelia stage of Basidiomycetes. The basidial stage is often designated by another name. *Rhizoctonia solani* (basidial stage: *Thanatephoris cucumeris*) is the most important member of this group which in particular affects cereals (wheat and oats), sunflower and cotton. *Rhizoctonia violacea* (basidial stage: *Helicobasidium purpureum*) is the causative agent of violet root rot. Colletotrichum spp. are associated with anthracnose disease in a number of plants. *Colletotrichum graminicola* affects cereals and grasses; *C. coccodes* affects vegetables including tomatoes and potatoes; *C. lagenarium* affects cucumbers and melons, in particular, and *C. lindemuthianum* affects Phaseolus bean.

Attempts have been made to control fungal infections of plants by biological means. For example, it is reported in Kommedahl and Mew, (1975) Phytopathology 65: 296–300, that three corn hybrids were coated with *Bacillus subtilis* and *Chaetomium globosum* to determine the effect on seedlings, final stands, stalk rot, and yields in the field, in comparison with the standard chemical seed treatment, captan. Stalk rot and breakage were less with the organism- and captan-coated seeds compared to non-coated seeds. Grain yields, however, were generally higher for the captan-coated seeds than for the organism-coated seeds. It was concluded that the organisms were not as consistent as captan in protecting the plants, and that additional research was required before the use of organisms for coating corn kernels would be commercially feasible. For additional discussion of biological control of fungal infections in plants see generally: R. J. Cook and K. F. Baker, *The Nature and Practice of Plant Pathogens* (Amer. Phytopathol. Soc. 1983); K. F. Baker and R. J. Cook, *BIOLOGICAL CONTROL OF PLANT PATHOGENS* (Amer. Phytopathol. Soc. 1982); Burges, H. D. (ed.) (1981)

*Microbial Control of Pests and Plant Disease* 1970–1980, Academic Press, New York; Baker, (1968) Ann. Rev. Phytopathol. 6: 263–294; Chang and Kommedahl, (1968) Phytopathology 58: 1395–1401; Kommedahl and Chang, (1966) Phytopathology 56: 885; Kommedahl et al., (1974) Ann. Proc. Am. Phytopathol. Soc. 1: 46; Mew and Kommedahl, (1972) Plant Dis. Rep. 56: 861–863; Mitchell, (1973) Soil Biol. Biochem. 5: 721–728; Papavizas, (1973) Soil Biol. Biochem. 5: 709–720.

In Kawamoto and Lorbeer, (1976) Plant Dis. Reptr. 60: 189–191, it is reported that onion seedlings were protected from damping-off, caused by a particular strain of *Fusarium oxysporum,* by infesting the onion seedlings with *Pseudomonas cepacia* Burkh strain 64–22. This *P. cepacia* strain (64–22) was reported to be recovered from the root, root-stem zone and seed coat on 18-day old seedlings from inoculated seeds. Live cells of *P. cepacia* 64–22 were reported to inhibit *Fusarium oxysporum* f. sp. *cepae,* while dead cells and culture filtrates did not. The authors stated that the mechanism through which *P. cepacia* protects young seedlings was open to speculation. The authors concluded that the experiments reported at least supported the feasibility of biological control measures to improve onion seedling stand, but that "at present we could not recommend infesting onion seed with *P. cepacia* for commercial plantings . . . ", presumably because some strains of *P. cepacia* have been reputed to be pathogenic to onions.

R. D. Lumsden reported in an abstract in Phytopathology 72: 709 (1982) that a strain of *P. cepacia* is antagonistic to *Pythium aphanidermatum* and protects cucumber seedlings from infection by this fungus in soil. In U.S. patent application Ser. No. 500,043, filed June 1, 1983, now U.S. Pat. No. 4,588,584, by R. D. Lumsden and Myron Sasser, they describe the protection of cucumber and peas from Pythium disease by use of a new biotype of *P. cepacia* designated SDL-POP-S-1. Protection is afforded through bacterial inoculation of seeds.

Another strain of *Pseudomonas cepacia* protected China Aster against wilt caused by *Fusarium oxysporum* f. sp. *callistephi* in greenhouse and field tests (T. D. Cavileer and J. L. Peterson, Abstract No. 522, American Phytophathological Society Annual Meeting, 1985).

Kommedahl and Mew, supra, also reported that captan is widely used as a seed treatment because it is reliable, easy to apply, and inexpensive. It was also reported, however, that captan is not always a good seed treatment under all conditions. In particular, Kommedahl and Mew, supra, reported that under prolonged conditions of low soil temperature and high soil moisture, biological controls proved superior to captan in reducing root infections. This was attributed to the possible multiplication of organisms and their growth from the seed to the root surface. Thus, despite the general effectiveness of captan and the lack of commercial prospects for biological control reported in Kommedahl and Mew, supra, it would be highly desirable to develop a method of biologically controlling fungal infections in cereal crops, particularly corn.

SUMMARY OF THE INVENTION

It is an object of the present invention to provide a method of biological control of fungal infection in plants.

It is another object of the present invention to provide biological control agents useful in methods of controlling fungal infections in plants.

Another object of the present invention is to provide methods of inoculating plants as well as bacterial strains useful in such methods, which protect plants from fungal infection and thereby enhance plant yields.

Still another object of the present invention is to provide bacterial strains which readily colonize the roots or rhizosphere of plants.

Yet another object of the present invention is to provide bacterial strains that colonize plant leaves.

A further object of the present invention is to provide a strain of a bacterium which readily colonizes a plant and can serve as a vector for the introduction to the plant of beneficial gene products produced by the bacterium.

In one embodiment the present invention provides methods and bacterial strains which protect corn plants from fungal infection and enhance corn yield.

In a specific embodiment the present invention provides substantially purified novel bacterial strains of *Pseudomonas cepacia* type Wisconsin. This type of *P. cepacia* is distinguished by the following characteristics:

i. ability to colonize leaves and roots of a variety of plants.
ii. broad spectrum antifungal activity.
iii. ability to protect plants which it colonizes from fungal disease, particularly a disease produced by a fungus of the genus Fusarium
iv. non-phytopathogenic.

In another embodiment the present invention provides a method of protecting a plant from a disease caused by a fungus comprising inoculating the plant with a strain of *Pseudomonas cepacia* type Wisconsin.

In yet another embodiment the present invention provides a bacteria containing agricultural inoculum suitable for inoculating a plant to introduce a bacterial strain into the plant rhizosphere, the plant roots or onto the plant surface comprising:

a. a suitable carrier that is non-phytotoxic, non-bacteriostatic and non-bacteriocidal; and
b. a bacterial strain that has the distinguishing characteristics of a *Pseudomonas cepacia* type Wisconsin strain.

In still another embodiment the present invention provides a composition of matter comprising a plant seed and a strain of *P. cepacia* type Wisconsin.

DETAILED DESCRIPTION OF THE INVENTION

Figure 1:
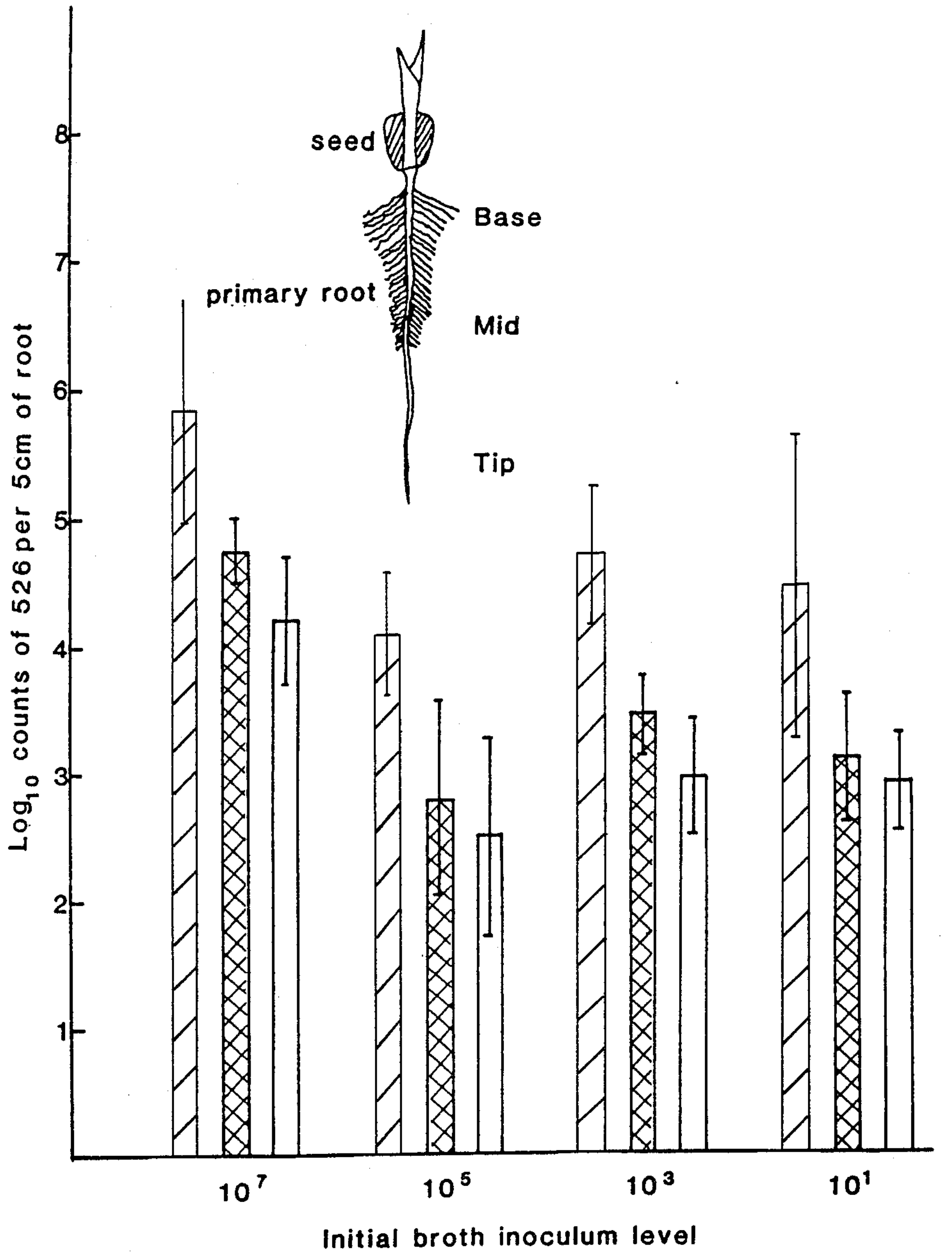
FIG. 1 is a graph showing the effect of seed inoculum size on recovery of rif-resistant *P. cepacia* strain 526 from 10 day old corn primary roots. Bacterial counts are given in $\log_{10}$ (cfu/5 cm of root). Bacterial counts were measured from the base, mid and tip sections of the primary root. Measurements from the base are indicated as shaded bars, those from the mid section by hatched bars, and those from the tip by unshaded bars. Inoculum size ranges from 10 to $10^7$ bacteria/seed.

The present invention describes the isolation and identification of diverse corn root colonizing bacteria from samples of corn root tissue and rhizosphere soil. Among these root-colonizing strains a number of non-fluorescent Pseudomonas strains, typed as belonging to the species *Pseudomonas cepacia,* were identified as good colonizers of the roots and rhizosphere of corn. It was discovered that a surprisingly large percentage of all the root-colonizing bacteria isolated were antagonists of the plant pathogenic fungus *Fusarium moniliforme.* A variety of bacterial strains including members of the genera Pseudomonas, Bacillus and Enterobacter were found to be antagonists of Fusarium. Among the fungal antagonist root-colonizing Pseudomonads, *P. fluorescens* and nonfluorescent *P. cepacia* were the most numerous.

Another surprising discovery of the present invention is the identification of a group of *P. cepacia* corn root-isolates which are good colonizers of both the root and/or rhizosphere of plants as well as colonizers of plant leaves. These strains where isolated from corn root samples but unexpectedly have an affinity for root colonization of diverse plants including sorghum, soybean, rape, cotton, tobacco and sunflower. More suprising is the ability of these bacteria to colonize leaves of diverse plants including tobacco, streptocarpus and cotton. In addition, these strains have been found to be broad spectrum fungal antagonists, with activity againt species of Phycomycetes (Pythium spp. and Phytopthora spp.), Ascomycetes (Sclerotinia spp. and Sclerotium spp.), Basidomycetes (Rhizoctonia spp.) and *Fungi imperfecti* (Fusarium spp. and Collectotrichum spp.).

Cell-free supernatant of a representative strain of this group, *P. cepacia* 526, have been shown to have activity against *Fusarium moniliforme, Saccharomyces carlsbergensis* and against the bacterium *Streptomyces aureofaciens.* Analysis of culture supernatant of *P. cepacia* 526 indicates the presence of at least three of four antibiotic substances. Two of these compounds have been identified as pyrrolnitrin and aminopyrrolnitrin which are known to have anti-fungal and anti-yeast activity and have previously been found to be produced by *P. multivorans* (now called *P. cepacia*) strains (Elander et al. (1968) Applied Microbiol. 16: 753–758). A third and possibly a fourth antibiotic component which have both anti-fungal and anti-yeast activity have not as yet been identified.

Further, strains of this type of *P. cepacia* have been found to protect plants which they colonize from fungal invasion and infection. In particular, these *P. cepacia* strains provide superior protection of corn from the pathogen *Fusarium moniliforme* when applied as a corn seed inoculant.

These effective plant colonizing strains of Pseudomonas have been identified as *Pseudomonas cepacia* using well established criteria summarized in Palleroni and Holmes (1981) Intl. J. System. Bacteriol. 31: 479–481 and Palleroni (1984) "Pseudomonadaceae" in *Bergey's Manual of Systematic Bacteriology,* Vol. 1, Krieg (ed.) Williams and Wilkins, London pp. 141–199. Unlike many plant isolated *Pseudomonas cepacia* strains, the organisms of the present invention are non-pathogenic to onions (Gonzalez and Vidaver (1979) J. Gen. Microbiol. 110: 161–170). To distinguish this group of related strains from known strains of *Pseudomonas cepacia,* the organisms of the present invention are designated *Pseudomonas cepacia* type Wisconsin. This type of *P. cepacia* is distinguished from other *P. cepacia* by the combined characteristics of good colonization of plant roots and/or rhizosphere and colonization of plant leaves, non-pathogenicity toward onion, broad spectrum fungal antagonism, and having the capability of protecting plants from infection and invasion by these fungi, particularly by fungus of the genus Fusarium.

The present invention provides substantially purified cultures of *P. cepacia* type Wisconsin. By "substantial purified" is meant a culture containing primarily only bacteria of the subject bacterial strain and free of contaminating microorganisms, particularly other strains of soil bacteria. Strains of *P. cepacia* type Wisconsin have the distinguishing characteristics noted above including the useful feature that they are effective colonizers of plant roots and leaves. These bacterial strains can then serve as vectors bringing to the plant any beneficial gene products of the strain. Such beneficial products could be those normally produced by the wild-type bacterium or the result of genetic alteration of the vector strain, for example, by simple mutation or the introduction of foreign genes. The Fusarium antagonist *P. cepacia* type Wisconsin wild-type strains are useful for providing Fusarium disease protection to the plants they colonize. Concurrently filed U.S. patent application (Stock et al. Ser. No. 891,305) describes the introduction of foreign genes encoding insect toxic protein into *P. cepacia* type Wisconsin strains and the successful use of these genetically altered strains to protect plants from insect larvae.

Specific embodiments of the present invention include the *Pseudomonas cepacia* type Wisconsin strains, listed in Table 1. The listed strains are independent isolates from different samples of corn root from several different fields having a history of use for corn cultivation at the Jacques seeds research farm near Prescott, Wis. (East half of the Northeast one fourth of Section 2, Township 26 North, Range 20 West, Pierce County, Wis., USA). All of these strains have the distinguishing characteristics of *P. cepacia* type Wisconsin. Strains of *P. cepacia* type Wisconsin are represented by two colony morphology types: mucoid and smooth including strains 406, 531 and 462 and mucoid becoming wrinkled with depressed center including strains 526 and 504. Representative strains *Pseudomonas cepacia* 526 and *Pseudomonas cepacia* 406 have been deposited with the American Type Culture Collection (ATCC), 12301 Parklawn drive, Rockville, Md. 20852, on Sept. 19, 1985, under the accession numbers ATCC 53266 and ATCC 53267, respectively.

TABLE 1

*Pseudomonas cepacia* type Wisconsin

| Strain[1] | Source[2] |
|---|---|
| 406 | site a, Jacques corn parental line 1, isolated originally on nutrient agar |
| 526 | site a, Jacques corn parental line 86, isolated on King's B medium |
| 462 | site a, Jacques corn parental line 13, isolated on combined carbon medium |
| 531 | site b, hybrid corn line 7780, isolated on King's B medium |
| 504 | site b, hybrid corn line 7780, isolated on combined carbon medium |

[1]All typed to *P. cepacia* using conventional criteria. See Palleroni and Holmes, 1981, and Bergey's Manual of Systematic Bacteriology VI (1984).
[2]Original root material was taken from test fields of Jacques Seed Company, Prescott, Wisconsin. Site a is the field of the experimental station which has been in continuous corn cultivation for 40 years. Site b is the demonstration planting field at the seed processing plant in Prescott, Wisconsin. Site a and site b are several kilometers apart.

TABLE 2

Inhibition of *Fusarium moniliforme* on Potato Dextrose agar (PDA) and King's B (KB) agar by rhizosphere bacteria (Representative isolates).

| Identified as | Strain No. | Origin[2] | Inhibition[1] on PDA | Inhibition[1] on KB |
|---|---|---|---|---|
| *Pseudomonas fluorescens* | 916 | Darling Downs (Qld) | + | + |
| " | SV44 | Salinus Valley USA | 0 | (+) |
| " | 608 | Wiconsin (USA) | 0 | + |
| " | 508 | Wisconsin (USA) | (+) | + |
| " | 611 | Wisconsin (USA) | + | + |
| *Pseudomonas putida* | 588 | Wisconsin (USA) | 0 | (+) |
| " | 963 | Darling Downs (Qld) | 0 | (+) |
| *Pseudomonas cepacia* | 406 | Wisconsin (USA) | + | (+) |
| " | 526 | Wisconsin (USA) | + | (+) |
| " | 64 | Kempsey (NSW) | + | + |
| " | 65 | Kempsey (NSW) | + | 0 |
| *Pseudomonas paucimobilis* | 56 | Kempsey (NSW) | 0 | 0 |
| Flavobacterium sp/CDC | 403 | Wisconsin (USA) | 0 | (+) |
| " | 1002 | Darling Downs (Qld) | 0 | (+) |
| Bacillus sp. | 1023 | Darling Downs (Qld) | + | (+) |
| " | 171 | Kempsey (NSW) | + | 0 |
| Actinomycetes | 1032 | Darling Downs (Qld) | (+) | (+) |
| *Enterobacter agglomerans* | 621 | Wisconsin (USA) | (+) | (+) |
| *Enterobacter cloacae* | 900 | Darling Downs (Qld) | (+) | 0 |
| Acintobacter sp. | 902 | Darling Downs (Qld) | (+)/0 | 0 |

[1]Inhibition of *Fusarium moniliforme*; + positive, (+) weak, 0 negative.
[2]Qld - Queensland
NSW - New South Wales

TABLE 3

Isolation of Pseudomonas *cepacia* Strains Antagonistic to *F. moniliforme* in vitro from Corn Roots Grown in Various Soils and Direct from Soil

| Soil Type or Location | Strain | Isolation History |
|---|---|---|
| 1a. Prescott, Wisconsin USA Jacques experimental field | 526[1] | Jacques parental line 86, unsterile root macerate on Kings B medium[2] |
| Silty loam | 406[1] | Jacques parental line 1, unsterile root macerate on combined carbon medium, 1983[2] |
| | 462[1] | Jacques parental line 13, unsterile root macerate medium.[2] |
| b. Prescott, Wisconsin USA | 504[1] | Jacques hybrid 7780, unsterile root macerate on combined carbon medium[2]. |
| Jacques demonstration field | 531[1] | Jacques hybrid 7780, unsterile root macerate on Kings B medium.[2] |
| 2. Kairi Queensland, Australia. Red-brown clay loam soil. | 285<br>349 | Cultivar QK487, on combined carbon,<br>Similar phenotype: yellow, fluorescent |
| 3. Kemsey, Frederick Town, New South Wales, Australia. Silty loam. | 6 | Cultivar GH5010, rhizosphere soil on nutrient agar 1983. |
| | 9 | CV GH5010, rhizosphere on soil. nutrient agar, 1983. |
| | 65 | CV GH5010, surface sterilized root macerate, strains 6,9, 65 similar phenotype: medium colony size, white, mucoid, 1983. |
| | 29 | CV GH5010, unsterile root macerate on nutrient agar, 1983. |
| | 69 | CV GH5010, root wash on nutrient agar, 1983, strains 29 and 69 similar phenotype: yellow, fluorescent. |
| 4. Tulia, Texas, USA | 790 | Cultivar Tender Treat. Spermosphere |

TABLE 3-continued

Isolation of Pseudomonas *cepacia* Strains Antagonistic to *F. moniliforme* in vitro from Corn Roots Grown in Various Soils and Direct from Soil

| Soil Type or Location | Strain | Isolation History |
|---|---|---|
| | | enrichment on nutrient agar, Phenotype: yellow, fluorescent, 1983. |

[1] *P. cepacia* type Wisconsin strains.
[2] Strains of *P. cepacia* type Wisconsin were reisolated from samples of soil taken from original root samples in Prescott, Wisconsin. These soil samples had been stored for 3 years under refrigeration.

TABLE 4

Inhibition of pathogenic fungi by various *Pseudomonas cepacia*

| Bacterial[b] Strain | Fungal strains[a] | | | | | | | | |
|---|---|---|---|---|---|---|---|---|---|
| | F119 | F120 | F130 | F110 | F111 | F112 | F100 | F104 | F113 |
| | Inhibition zones[c] | | | | | | | | |
| 526 | 4 | 4 | 5 | 2 | 4 | 3 | 3 | 1 | 4 |
| 406 | 4 | 4 | 5 | 2 | 4 | 3 | 3 | 1 | 3 |
| 64 | 4 | 4 | 5 | 3 | 5 | 3 | 3 | 1 | 4 |
| 65 | 2 | 4 | 5 | 2 | 2 | 2 | 1 | 1 | 2 |
| 285 | 3 | ND | ND | ND | 1 | 1 | 1 | ND | ND |
| 29 | 2 | ND | ND | ND | 1 | 1 | 2 | ND | ND |
| 790 | 3 | ND | ND | ND | 0 | 0 | 1 | ND | ND |
| 25416 | 3 | ND | ND | ND | 0 | 0 | 1 | ND | ND |
| 29424 | 5 | ND | ND | ND | 4 | 3 | 2 | ND | ND |
| 17460 | 5 | ND | ND | ND | 1 | 2 | 2 | ND | ND |
| 10856 | 0 | ND | ND | ND | 0 | 0 | 0 | ND | ND |
| 17616 | 0 | ND | ND | ND | 0 | 0 | 0 | ND | ND |
| 17759 | 0 | ND | ND | ND | 0 | 0 | 0 | ND | ND |

[a] Fungal strains; F119 *Fusarium moniliforme*, F120 and F130 *Fusarium graminearum*, F110 *Fusarium oxysporum*, F111 and F112 *Sclerotinia sclerotiorum*, F100 *Macrophomina phaseolina*, F104 *Colletotrichum lindemuthianum*, F113 *Rhizoctonia solani*.
[b] *P. cepacia* strains 526, 406, 64, 65, 285, 29, and 790, isolated from maize rhizosphere and roots; the rest were ATCC strains.
[c] Measured as described in Example 2 in mm; assays performed on potato dextrose agar; ND = not determined.

All bacteria isolated as described in Example 1, were screened initially, as in Example 2, for antagonism against the fungus *Fusarium moniliforme*. As shown in Table 2, strains identified as *P. fluorescens*, *P. cepacia*, *Bacillus* sp., *Actinomycetes* and *Enterobacter agglomerans* displayed anti-fungal activity against this Fusarium. Fusarium antagonist *P. cepacia* strains were obtained from many samples assayed (Table 3). *P. cepacia* root-isolates were assayed using in vitro plate assays for inhibition of a wider group of fungi, as shown in Table 4. In each case, *P. cepacia* root-isolates had antifungal activity against at least one other fungus tested. *P. cepacia* type Wisconsin strains 526 and 406 were particularly effective as broad spectrum fungal antagonists. In addition to *Fusarium moniliforme*, *P. cepacia* 526 and 406 were active against the plant pathogens *F. graminearum*, *F. oxysporum*, *Sclerotinia sclerotiorum*, *Macrophomina phaseoli*, *Colletotrichum lindemuthianum* and *Rhizoctonia solani* (Table 4). In further assays, *P. cepacia* 526 and 406 were also found to be antagonists of *Phytophthora cinnamomi*, *Pythium ultimum*, *Sclerotium rolfsii* and *Verticillium dahliae*. Included in Table 4 are six ATCC strains of *P. cepacia* for comparison to root isolates; only one half of these strains displayed any anti-fungal activity. In the ATCC strains tested, fungal antagonism was not found to be correlated with the environmental origin of the strain.

Plant pathogenicity was herein assessed as pathogenicity to onion bulb tissue because of the known association of many *P. cepacia* strains with onion. *P. cepacia* strains were assessed for onion pathogenicity by inoculation of onion tissue as described in Example 8. Isolates with socres of 2 or more are considered to be pathogenic strains. As shown in Table 8, some of the *P. cepacia* (not type Wisconsin) root-isolates were onion pathogens, particularly strain 64. The *P. cepacia* type Wisconsin stains 526 and 406 were not found to be significantly pathogenic to onion tissue.

A microorganism that is isolated from a particular environment is considered to colonize that environment. Thus bacteria isolated from plant roots are root-colonizing bacteria. The ability of a bacterium to colonize a particular environment can also be assessed as the ability of the bacterium to proliferate or persist in that particular environment after introduction. Thus a bacterium that becomes established and persists on leaf tissue after inoculation, is considered to colonize leaf tissue. The relative ability of bacterial strains to colonize a particular environment can be measured in experiments like those described in Examples 3, 4 and 7. For comparative purposes in this application tested isolates that were recoverable from plant root or rhizosphere (at two weeks, Example 3) at a level of greater than or equal to about $10^6$ bacteria/g root or soil were considered good root and/or rhizosphere colonizers; those recovered at levels between about $10^5$–$10^6$ as average colonizers and those recovered at levels below about $10^5$ as poor colonizers. Using these criteria, root-isolate Fusarium antagonist strains of *P. cepacia*, including *P. cepacia* type Wisconsin strains 526 and 406 were categorized as good root and/or rhizosphere colonizers.

*P. cepacia* 526 is found to colonize the tip, mid and base sections of the root after seed inoculation (FIG. 1). High levels of *P. cepacia* 526 are recovered from unsterile root macerate, root wash and rhizosphere soil, suggesting general colonization of the whole rhizosphere. At two weeks, after seed inoculation, *P. cepacia* 526 is not only recovered in high numbers from roots of inoculated plants but it is shown to be the dominant (about 99%) aerobic heterotroph isolatable from macerated root.

Figure 2:
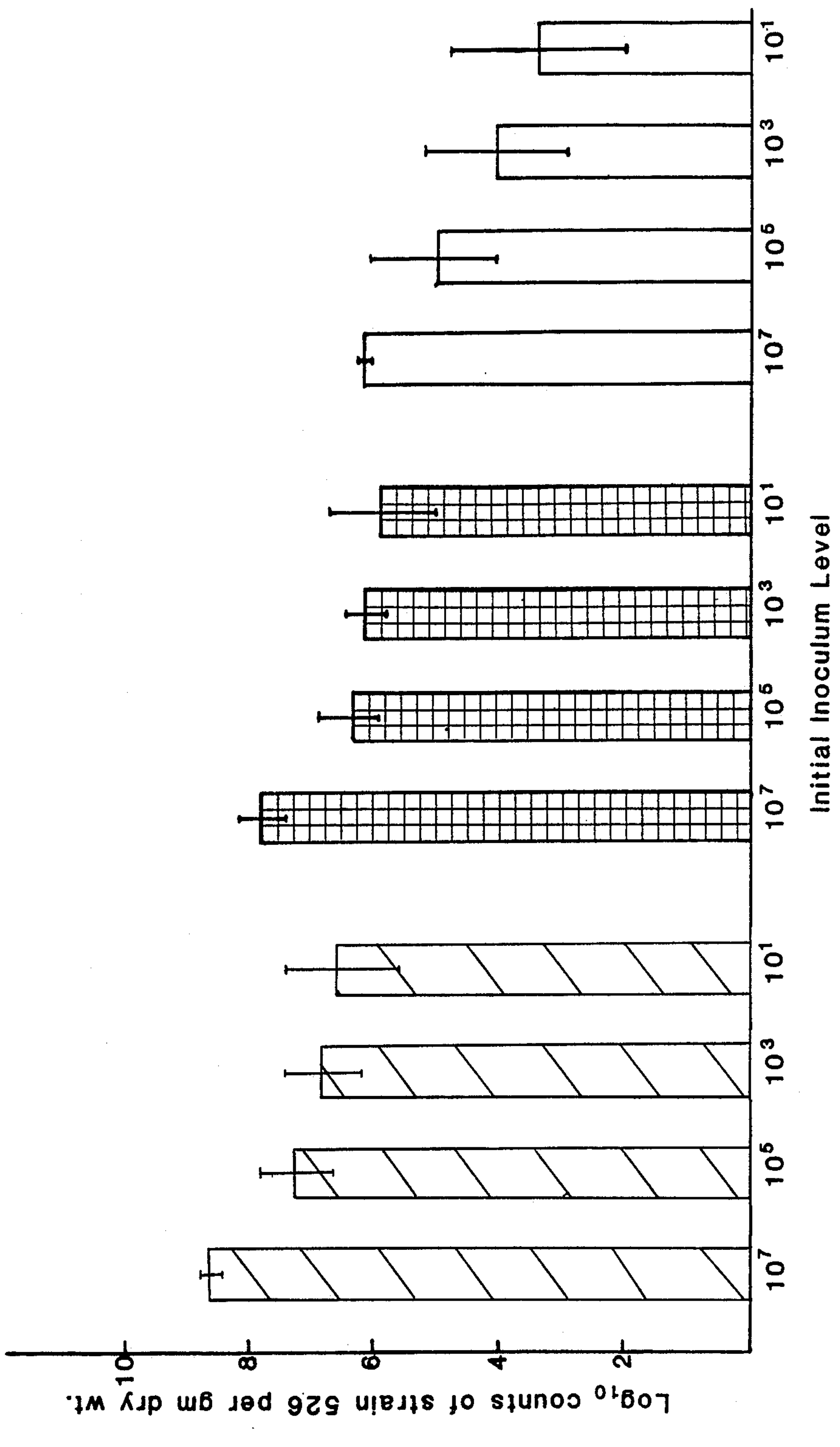
FIG. 2 is a graph showing the relationship between inoculum size and the recovery of *P. cepacia* strain 526 from the rhizosphere of 2 week old corn plants. Bacterial counts are given in $\log_{10}$ (cfu/g dry weight root or soil). Inoculum size ranges from 10 to $10^7$ bacteria/seed. Bacterial counts were measured in the root wash (shaded bars), root macerate (hatched bars) and in rhizosphere soil (unshaded bars).

Successful colonization of corn roots by *P. cepacia* 526 can be accomplished from seed inoculum levels as low as 10 bacteria/seed (FIGS. 1 and 2). This is much lower than levels of bacterium usually applied in such inocula ($10^7$ to $10^8$ bacteria/seed).

A comparison of root colonizing ability of the good root colonizer *P. cepacia* 526 to that of six ATCC *P. cepacia* strains (results listed in Table 9 and in FIG. 6) indicates that all of the ATCC strains tested were good to average colonizers of corn root and/or rhizosphere. To applicants' knowledge none of the tested ATCC strains is reported to be a root-isolate. ATCC strains 29424 and 17616 are at least equivalent to *P. cepacia* 526 in colonization ability. *P. cepacia* type Wisconsin strains 526 and 406 were found to colonize roots of a variety of plants (Table 5). These strains are good colonizers of corn, sorghum, sunflower, alfalfa, cotton, pea and tomato and average colonizers of rape and soybean. The persistence of these strains on roots is relatively good except for alfalfa and tomato, in which 526 and 406 population decreases significantly with time.

TABLE 5

| Populations of *P. cepacia* type Wisconsin (526 and 406) recovered from roots of crop plants following seed inoculation | | |
|---|---|---|
| | Population size (Log$_{10}$ *P. cepacia* cells/g dry wt root[a]) Plant age | |
| Plant species | 2 weeks | 2 months |
| Corn cv | | |
| JX 47 | 7.64 | 5.35 |
| JX 97 | 7.62 | 5.04 |
| JX 167 | 7.69 | 5.49 |
| JX 180 | 7.49 | 5.53 |
| Sorghum TE | 7.46 | 4.47 |
| Oil seed rape | 5.84 | 4.45 |
| Sunflower | 6.89 | 4.31 |
| Wheat | 6.32 | 4.69 |
| Alfalfa | 6.71 | 1.33 |
| Cotton | 7.42 | 4.43 |
| Soybean | 5.11 | 3.58 |
| French bean | 5.83 | 5.11 |
| Peas | 7.31 | 6.37 |
| Tomato | 7.03 | 2.11 |

[a]Values are the means over two soil types and two *P. cepacia* inoculum strains (526 and 406). Initial inoculum level was about $10^7$/seed.

A surprising finding of the present application is that the good root-colonizing *P. cepacia* type Wisconsin strain 526 is also a colonizer of plant leaves. Leaf colonization ability was assessed as described in Example 7. *P. cepacia* 526 has been found to colonize leaves of tobacco, cotton and streptocarpus plants. The ability of strain 526 to colonize leaves of such diverse plants, suggests that its leaf colonizing ability is general to many plants.

Figure 3:
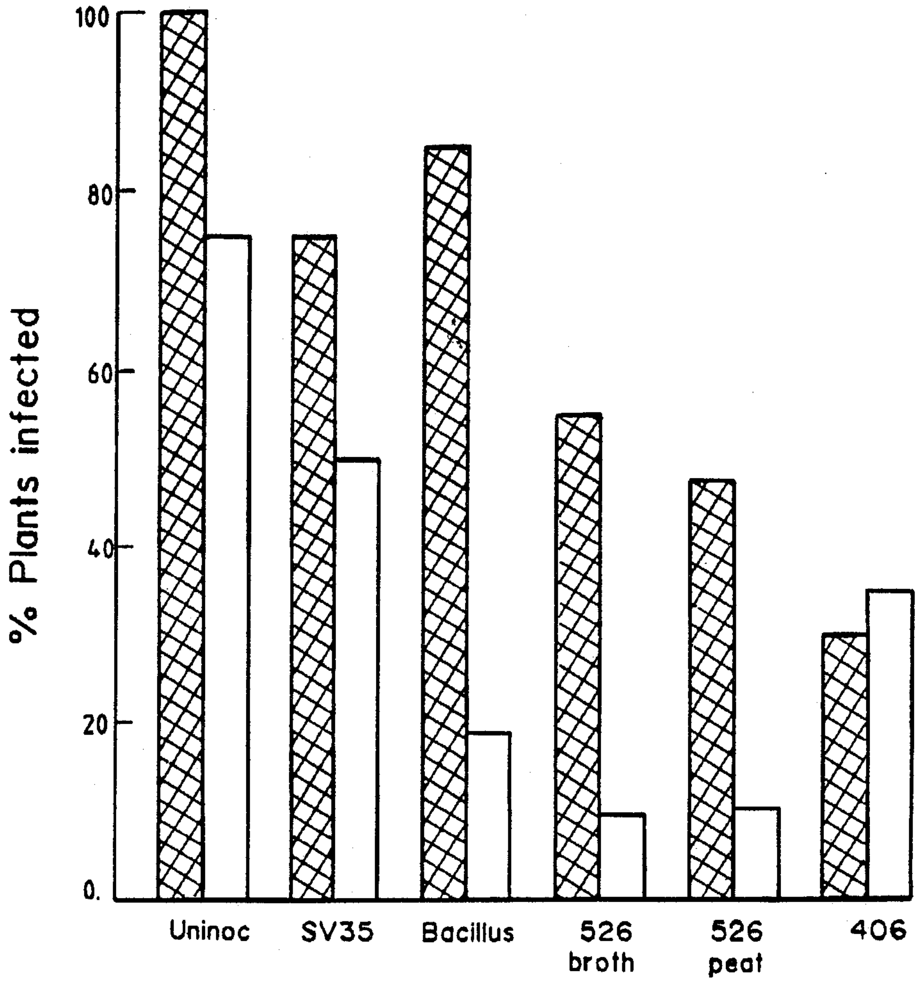
FIG. 3 is a graph showing the effect of seed inoculants on the amount of *F. moniliforme* infection of 2 week old corn shoots. Pieces of the stem base (mesocotyl) and growing point (plumule) were assayed for fungal invasion. Hatched bars represent measurements from the mesocotyl and unshaded bars represent measurements from the plumule.
Figure 4:
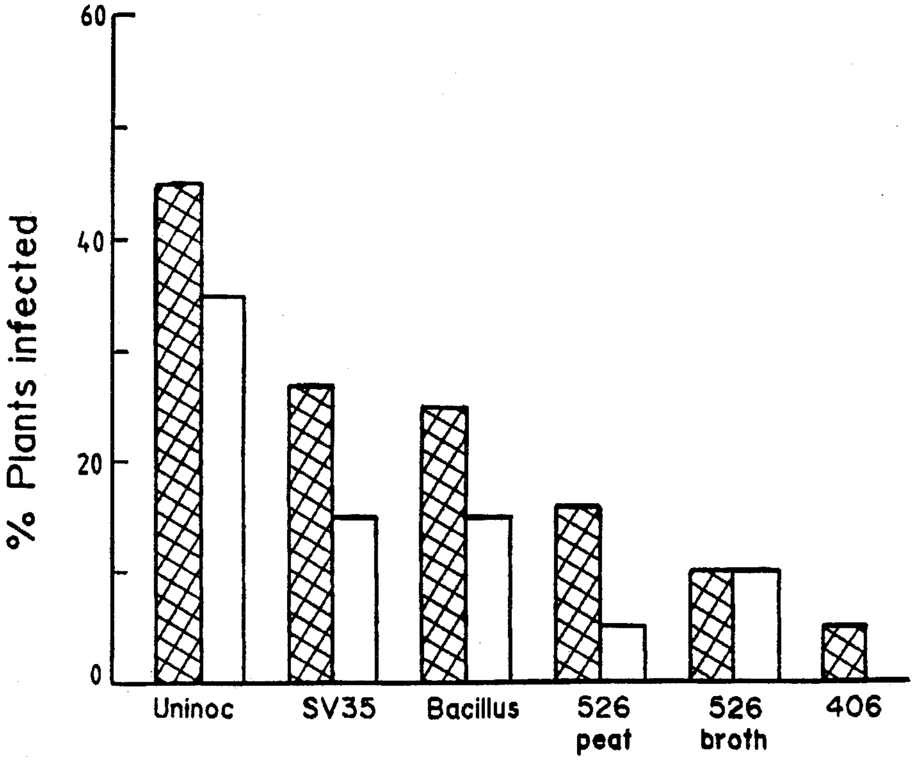
FIG. 4 is a graph showing the effect of different seed inoculants on the amount of total fungal infection of 2 week old corn shoots. Pieces of the stem base (mesocotyl) and growing point (plumule) were assayed for fungal invasion. Hatched bars represent measurements from the mesocotyl and unshaded bars represent measurements from the plumule.

Protection of plants from fungal infection and invasion has been assessed herein using plate assays of fungal invasion of plants grown from seeds inoculated with test bacteria (Example 5, FIGS. 3–5 and Table 4). *P. cepacia* strains 526, 406 and 64 were found to protect corn plants from invasion and infection by *Fusarium moniliforme.* Seed inoculation by both *P. cepacia* 526 or 406 was found to protect both roots and stems of plants from fungal invasion. In comparison to a number of *P. cepacia* strains, the *P. cepacia* type Wisconsin strains (FIG. 6, Table 7) are found to be superior plant fungal protection agents, when applied for example as seed inocula. Superior protection is herein assessed as greater than 50% protecion from Fusarium invasion as determined by the methods of Example 5.

A possible explanation for the superior protection afforded plants by inoculation with strains 526 and 406 is the combined fungal antagonism and good root colonization ability of these stains. However, the simple combination of antifungal activity and good root colonizing ability does not in all cases result in superior protection from fungal invasion. For example, *P. cepacia* ATCC strain 25416 combines good colonizing ability for corn root and Fusarium antagonism, but does not afford superior protection of plants. In contrast, for example, *P. cepacia* ATCC strain 17616 provides significant protection from Fusarium invasion, albeit less than 526 and 406, even though this strain displays no anti-Fusarium activity. It is believed that colonization ability is requisite for a strain to be capable of protecting a plant on which it is inoculated from fungal invasion and infection. Fungal antagonism at least as determined by in vitro plate inhibition assays, is not absolutely requisite for a strain to provide a plant with fungal protection. The ability of a bacterial strain to protect a plant from fungal invasion is thus an independent property useful for strain characterization.

Figure 6:
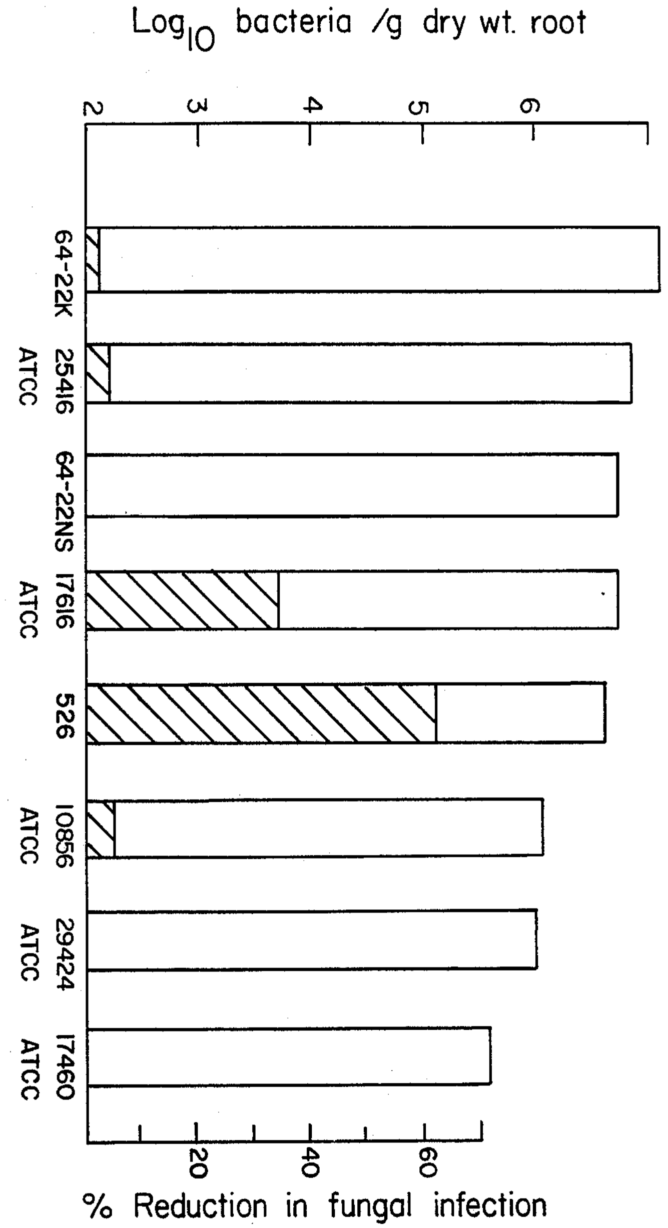
FIG. 6 is a graph comparing root colonization and reduction of fungal infection (*Fusarium moniliforme*) by seed inoculation of eight *P. cepacia* strains including *P. cepacia* Wisconsin 526. Bacterial counts of roots are indicated by unshaded bars. The percent reductions in fungal infection are indicated by hatched bars. The SED is 0.42 in these measurements.

Anti-fungal activity, corn root colonization, corn protection from Fusarium infection and onion pathogenicity of *P. cepacia* root isolates and ATCC *P. cepacia* strains are compared in Table 8 and FIG. 6. *P. cepacia* type Wisconsin strain 526 is shown to be distinct from those *P. cepacia* strains tested. It is distinguished from the 64-22 strains as nonpathogenic to onions. *P. cepacia* strain SDL-POP-S-1 (which was reported by Lumsford and Sasser (U.S. patent application No. 500,043, filed June 1, 1983) to be a Pythium antagonist) has been found to be distinct from *P. cepacia* type Wisconsin strain 526 and 406. Strain SDL-POP-S-1 produces a diffusible pigment which fluoresces (yellow-green) under UV light and does not inhibit *F. moniliforme* in in vitro plate assays.

Root-colonizing fungal antagonist bacterial strains are reproducibly isolated by applying the screening methods of Example 1 and 2. An important but not limiting factor in the initial isolation of large numbers of fungal antagonists is believed to be the choice of corn root and corn field soil samples from fields that had been under cultivation for corn for many years. For example, the cornfield at Jacques experimental station had been under continuous cultivation by corn for forty years. The fact that root-colonizing fungal antagonist bacterial strains are readily isolatable from diverse geographic locations, suggests that these organisms are widely dispersed.

*P. cepacia* root-colonizing fungal antagonists, including strains distinguished as *P. cepacia* type Wisconsin can also be readily and reproducibly isolated from the root and/or rhizosphere soil samples by initial dilution plating of samples on a *P. cepacia* selective medium. One such medium has been described by Burbage et al. (1982) Phytopathology 72: 706. Root-colonizing *P. cepacia* selected in this initial plating are then screened, as in Example 2, for anit-fusarium activity. In principle, any fungus could be employed in this screen. The resultant selections are *P. cepacia* root-colonizing fungal antagonists. It is preferred that colonization ability and fungal protection of the resultant isolates be confirmed.

This selection/screening method has been applied to reisolate *P. cepacia* type Wisconsin strains from the Prescott, Wisc. cornfield soils used in the original isolation. This soil sample had been stored under refrigeration for over three years. Seven isolates, identified by biochemial, nutritional and other criteria as *P. cepacia* strains, were obtained by selective plating. All of these isolates are inhibitory to *Fusarium moniliforme* on in vitro plate assays and among these isolates there is at least one strain that has the distinguishing characteristics of *P. cepacia* type Wisconsin.

A primary use of the bacteria in the present invention is the inoculation of a plant to impart some benefit to the plant, such as the inhibition of fungal disease caused by Fusarium fungi. Since the bacteria of the present invention are colonizers of the rhizosphere and/or root tissue of plants, it is only necessary that they be applied in the vicinity of the seed or young plant, sufficiently close to establish colonization. It is preferred that the bacterial strains of the present invention be applied in the vicinity of the seed at the time of planting in order to establish root colonization. This can be accomplished by either direct or indirect inoculation of seeds at the time of planting.

By direct inoculation is meant that the bacterial inoculant is applied directly to the seed prior to sowing it in the field. In its simplest form, this can be spraying the seed with or dipping the seed into a liquid culture containing a strain of the present invention. This results in a plant seed coated with a composition containing the bacterium. A preferred method of direct inoculation is to pellet the seed with a carrier containing the desired *P. cepacia* strain. Generally, the bacterium is applied to a carrier and then a pellet is formed with the carrier surrounding the seed. Numerous, diverse carriers are known to those of skill in the art and include, but are not limited to, peat, soil, calcium carbonate (many forms), dolomite, gypsum (various grades), bentonite (and other clay minerals), rock phosphates (and other phosphorous compounds), titanium dioxide, humus, talc, alginate and activated charcoal. Any agriculturally suitable carrier known to one skilled in the art would be acceptable. Often, it is desirable to include an adhesive in the pellet to hold the bacterium-containing carrier to the seed. While the art is also aware of numerous acceptable adhesives, some of them include, but are not limited to, synthetic glues, glues of vegetable origin (such as gum arabic), gelatin, various sugars, and bee honey. In general, the solid carrier should be close to neutral pH and finely ground (i.e., at least about 90% passing through 300 mesh). Pelleted seed containing the microoganism of the present invention can be directly sown in the field.

A typical inoculant of the present invention is prepared by mixing gum arabic (30% w/v) with the bacterial strain in a finely ground (to pass 300 mesh) peat carrier. This mixture is then mixed with seed, for example, at the rate of 400 g per 20 kg of seed, or enough seed to plant 1 hectare.

An alternative to direct seed inoculation is indirect seed inoculation; i.e., an agricultural inoculum containing a bacterium of the present invention in a suitable carrier is introduced into the vicinity of the seed at the time of sowing. The carrier can either be solid or liquid, many being known to those of skill in the art. The basic requirement is that the carrier neither be phytotoxic, bacteriostatic, nor bacteriocidal. An example of a liquid agricultural inoculum is simply a *P. cepacia* type Wisconsin strain of the present invention in a liquid growth medium, which is sprayed into the row as the seed is planted. Solid carriers can comprise many of the materials indicated as being suited for pelleting seed. For example, a popular method is to employ peat suspended in water as a carrier of the bacterium, and spray this mixture into the row in the furrow beside and over the seed as it is planted. Another example of a solid agricultural inoculum is granules comprised of calcium sulfate hemihydrate and carboxymethylcellulose sprayed with a bacterial broth. Yet another example of a solid inoculant is granulated peat inoculated with a bacterium which is run into the seed furrow at planting in the vicinity of the seed. Other examples of solid inoculant are quartz sand and marble chips coated with a peat culture of the bacterium. It is also known to include nutrients, such as powdered milk or sucrose, in the solid inoculant granules.

The *P. cepacia* type Wisconsin strains of the present invention also colonize plant leaves and thus are useful also as vectors to target beneficial products to plant leaves. In order to establish a leaf-colonizing strain on leaf tissue, it is necessary to inoculate leaves with an appropriate agricultural composition containing the desired strain. Such foliar inoculants can be applied, in principle, at any time during growth of the plant. A particularly useful method of inoculating plant leaves is by spraying, either liquid or particulate inoculating compositions onto plant leaves.

Inoculating compositions suitable for spraying generally include a sprayable agricultural carrier such as water which contains viable cells of the desired bacterial strain. Often, it is desirable to include wetting, emulsifying and sticking agents to improve application. It may be desirable also to include bacterial nutrients or other additives which enhance retention of inoculum viability. Again, all components of such a composition must be non-toxic to plants and the bacterial inoculant, and further must not inhibit bacterial growth (bacteriostasis) nor injure plant foliage.

The present invention contemplates that those of the ordinary skill in the art are familiar with the basic techniques of agricultural inoculation. See, e.g., Brockwell in *Methods for Evaluating Biological Nitrogen Fixation,* pp. 417–488 (F. J. Bergersen ed. 1980); Burton in *Biological Nitrogen Fixation Technology for Tropical Agriculture,* pp. 105–114 (P. H. Graham and S. Harris eds. 1982); Roughley in Ibid., pp. 115–127; Brockwell in *Nitrogen Fixation in Legumes,* pp. 211–227 (J. M. Vincent ed. 1982); Kremer et al., (1982) Soil Sci. Soc. Am. J. 46: 539–542; Kremer et al., (1983) Appl. Env. Microbiol 45: 1790–1794; Brockwell, (1962) Aust. J. Agr. Res. 13: 638–649; Bergersen et al., (1958) J. Aust. Inst. Agric. Sci. 24: 158; Hastings et al., (1962) N. Z. J. Agr. 104: 330; Fraser, (1966) J. App. Bacteriol. 29: 587–595; Schiel et al., (1970) Rev. Invest. Agrospec. Ser. 2 7: 239; Iswaran et al., (1971) Zentralbl. Bakteriol. Parasitenk. Infektionskr., Abt. II, 126: 43; Iswaran et al., (1971) Zentralbl. Bakteriol. Parasitenk Infektionskr., Abt. II, 126: 45. Modifications of the examples below will be apparent to those of skill in the art, it is intended that this invention be limited only by the scope of the appended claims.

EXAMPLE 1

Isolation of rhizosphere bacteria

This example demonstrates the isolation of bacteria from the rhizosphere soil and roots of corn plants.

Corn roots and corn field soil were harvested from several geographical locations (Table 3), different sites within these locations and different corn plant cultivars. Within these locations both old and young root samples were taken. Samples of corn roots and the accompanying loosely attached rhizosphere soil were individually bagged and transported to the Genetics Department, Research School of Biological Sciences, Australian National University, Canberra, Australia, where subsampling and isolation procedures were performed.

The following subsampling procedures were performed:

Rhizosphere soil—soil loosely attached to the roots which can be shaken off.

Simple root wash—soil is removed by thorough washing under running tap water.

Extensive root wash—after the rhizosphere soil is shaken off, roots (2–5 g) were transferred to 100 ml of sterile Fahraeus nutrient solution with 20 gms of 2 mm glass beads, and shaken for 15–20 minutes at 250 rpm in an orbital shaker.

Unsterilized root macerate—roots, after either root wash treatment, were macerated in 100 ml of sterile Fahraeus nutrient solution with a blender for 30–40 seconds.

Sterilized root macerate—time required for surface sterilization differed for old roots and for roots from 2 week old seedlings:

a. For old roots—Roots, after root wash treatments, were surface sterilized in 3% hydrogen peroxide (BDH Analar) for 10 minutes under constant shaking at 250 rpm, followed by 3–4 washings in sterile water. The roots were then transferred to 4% sodium hypochlorite (BDH) and surface sterilized for 30 minutes under constant shaking at 250 rpm. Roots were then washed in sterile water 3–4 times to remove the residual hypochlorite before being macerated.

b. For young roots—The same as above, except the roots were surface sterilized in 3% hydrogen peroxide for 10 minutes followed by 15 minutes in 4% sodium hypochlorite. The efficiency of surface sterilization is checked by performing a roll test on a nutrient agar plate.

Root washings and root macerates were serially diluted in 4.5 ml Fahraeus medium (Vincent (1970), *A Manual for the Practical Study of Root Nodule Bacteria*, Blackwell) and 0.1 ml was plated onto nutrient agar (NA, Difco) (1.5% agar, pH 6.8–7.0), King's B medium (1.5% agar, pH 7.2) (King et al. (1954) J. Lab Clin. Med. 44: 301–307), and complex carbon medium (Rennie (1981) Can. J. Microbiol. 27: 8–14) at dilutions $10^4$ to $10^8$. The plates were incubated at 30° C.–33° C. for 48 to 72 hours and colonies counted. Most aerobic heterotrophic soil bacteria grow on nutrient agar while King's B Medium is selective for fluorescent pseudomonads. Distinct bacterial isolates were selected from these platings by selecting colonies of different colony morphology types. Selections were purified by streaking on NA and the purified selections were stored in NA stabs at room temperature and 4° C. Bacterial counts (NA) were found to be the highest in root wash and unsterile root macerate treatments (approximately $10^9$ cfu/gram dry weight root). These subsamples are the preferred source of root colonizing bacteria.

The following media were employed in the isolation and/or screening of bacteria isolates:

| | |
|---|---|
| Nutrient Agar | |
| Nutrient broth (Difco) | 8 g |
| Agar | 15 g |
| Water (deionized) | 10000 ml |
| pH 6.8–7.0 | |
| King B Medium (King, et al., 1954) | |
| Protease peptone (Difco) | 20 g |
| Glycerol | 8 ml |
| $K_2HPO_4.3H_2O$ | 1.5 g |
| $MgSO_4.7H_2O$ | 1.5 g |
| Agar purified (Oxoid) | 15 g |
| Water (deionized) | 1000 ml |
| pH 7.2 | |

Fahraeus Medium (Vincent, 1970 A Manual for the Practical Study of Root-Nodule Bacteria, Blackwell)

| | mg/l |
|---|---|
| $CaCl_2.2H_2O$ | 100 |
| $MgSO_4.7H_2O$ | 120 |
| $KH_2PO_4$ | 100 |
| $Na_2HPO_4.12H_2O$ | 150 |
| Ferric citrate | 1.5 m |
| Trace element solution | 1 ml |

-continued

| | |
|---|---|
| pH 6.5 | |

Trace element solution (Gibson (1963) Aus. J. Biol. Sci. 16:28–42)

| | g/l |
|---|---|
| $H_3BO_3$ | 2.86 |
| $MnSO_4.4H_2O$ | 2.08 |
| $ZnSO_4.7H_2O$ | 0.22 |
| $CuSO_4.5H_2O$ | 0.08 |
| $H_2MoO_4.H_2O$ | 0.09 |

EXAMPLE 2

This example demonstrates the screening of the rhizosphere isolates of Example 1 for inhibition of growth of Fusarium fungi.

Purified rhizosphere isolates were spotted onto King's B and Potato Dextrose agar (Difco) plates with a toothpick and incubated at 30° C.–33° C. to allow establishment of the bacterial isolates. After 24 hours, the plates were sprayed with a spore suspension of *F. moniliforme* using a perfume sprayer. The spore suspension was prepared by shaking carnation leaf pieces infested with *F. moniliforme* in 10 ml of sterile water. Spore inoculated plates were then incubated at 28° C. for 48–72 hours and bacterial isolates showing a fungus-free zone around them were scored as positive for Fusarium inhibition. Inhibition ranged from weak, where the fungal mycelium did not grow over the bacterial spot, to strong where there was 3–6 mm zone of inhibition surrounding the bacterial spot.

The percentage of bacterial isolates showing inhibition of *F. moniliforme* varied depending upon the soil from which they were isolated. Thirty-seven percent of Darling Downs isolates, 20% of Wisconsin isolates, 29% of Kempsey isolates and 11% of Kairi isolates showed plate inhibition of *F. moniliforme.*

Using conventional criteria such as colony morphology, Gram staining and a range of biochemical tests (for example, API-Zone—analytical profile index), rhizosphere isolates showing Fusarium antagonism were typed. Table 2 gives a representative list of Fusarium inhibitory bacteria isolated from the corn roots from different soils. Inhibition on plates varied depending upon the medium used. A few strains, *Pseudomonas fluorescens* (916, 611 and 508), *Pseudomonas cepacia* (526, 406, 64), Bacillus sp. (1023) and Actinomycetes (1032), showed inhibition on both Potato Dextrose and King's B agar. The spectrum of inhibitory bacteria varied according to soil type. Table 6 lists these types and their levels in some of the different soils studied. Corn root isolates from Wisconsin soils demonstrated high levels of several species of Pseudomonas.

Inhibition is presumably due to the production of some inhibitory substance by the microorganism.

TABLE 6

Counts of bacteria antagonistic to *Fusarium moniliforme* from roots and rhizosphere of corn plants.

| Strain Identified as | Inhibition[1] | Counts/gm fresh wt from Wisconsin | Kemspey | Darling Downs |
|---|---|---|---|---|
| *Pseudomonas putida* | (+) | $10^6$ | $10^7$ | $10^7$ |
| *Pseudomonas fluorescens* | + | $10^8$ | $10^7$ | $10^7$ |
| *Pseudomonas cepacia* | + | $10^8$ | $10^6$ | ND |
| Flavobacterium | (+)/0 | $10^8$ | $10^7$ | $10^7$ |
| Bacillus | + | ND | $10^8$ | $10^3$ |
| Actinomycetes | (+) | ND | ND | $10^4$ |
| Acinetobacter | (+)/0 | ND | ND | $10^7$ |

TABLE 6-continued

Counts of bacteria antagonistic to *Fusarium moniliforme* from roots and rhizosphere of corn plants.

| Strain Identified as | Inhibition[1] | Counts/gm fresh wt from Wisconsin | Kemspey | Darling Downs |
|---|---|---|---|---|
| Enterobacter | (+)/0 | $10^6$ | ND | $10^7$ |

ND = not detected
[1]Inhibition of *Fusarium moniliforme*; + positive, (+) weak, 0 negative, (+)/0 some isolates weak, others negative.

EXAMPLE 3

Rhizosphere colonization screen

This example demonstrates a screen for root or rhizosphere colonization ability applied to Fusarium antagonists identified in Example 2.

In order to score colonization by bacteria, it was necessary to employ strains with a selectable marker. Spontaneous rifampicin resistant mutants of bacterial isolates showing inhibition of *F. moniliforme* on plates were selected at concentrations of 50 to 100 μg rifampicin/ml. The spontaneous rifampicin resistant mutants were checked for retention of antifungal activity before root colonization tests were performed.

For colonization pot trials, corn seeds were surface sterilized with 4% sodium hypochlorite for 20 to 30 minutes and washed 3-4 times with sterile water. The seeds were pre-germinated on semi-solid Fahraeus Medium (0.5%) agar (Vincent, 1970) for 24 hours at 33° C. Seeds were either broth or peat inoculated. For broth inoculation, the pre-germinated seeds were soaked in a late log phase nutrient broth culture (ca. $1\times10^9$/ml) for 10-15 minutes and sown in 25 cm pots filled with soil watered to field capacity. For peat inoculation, seeds were coated with a slurry made by mixing 1 g of a peat culture of the antagonistic bacteria and 1.5 g of a sticker solution (1.1 g methyl cellulose of 60 ml water). Seeds were then sown in pots as above.

Rhizosphere soil, root washings, and root macerates from 2 week and 2 month old corn plants from inoculated seeds were plated on selective medium (nutrient agar plus rifampicin at 100 μg/ml) and counts taken after 48-72 hours of incubation. The bacterial isolates were classified as good or poor colonizers depending upon their recovery from corn rhizosphere soil and roots. Isolates recovered at levels less than about $10^5$/gm root or soil are considered poor colonizers, about $10^5$-$10^6$ as average colonizers, and about $10^7$-$10^8$/gm root or soil as good colonizers. Most bacterial isolates showed fairly good colonization after the first 2 weeks of growth but their numbers declined after 2 months. *Pseudomonas cepacia* 406 and 526, and *Enterobacter agglomerans* 621 showed good colonization while *Enterobacter cloacae* 900, Flavobacterium 403 and 1002, *Pseudomonas fluorescens* A12, 508, 608 and 976, *Pseudomonas putida* 920 and 963, and Acinetobacter 902 were medium to poor colonizers. *Pseudomonas fluorescens* 916, Bacillus and Actinomycetes were poor colonizers. The strains *P. cepacia* 406 and 526 were selected for further study and characterization.

EXAMPLE 4

Root or Rhizosphere Colonization Assays

This example demonstrates the efficiency of colonization in a competitive situation for one of the strains identified as a good colonizer in Example 3, *P. cepacia* 526. The tests of Example 3 showed *P. cepacia* to be a good colonizer of corn when inoculated at relatively high levels. The following experiments examine the variation of colonizing ability of *P. cepacia* 526 as a function of inoculum size. These experiments assay how well *P. cepacia* 526 will compete for root colonization with natural soil isolates.

Corn seeds were dipped for 5-10 minutes in broth cultures of the rif-resistant mutant of *P. cepacia* 526 which were adjusted to $10^7$, $10^5$, $10^3$ and $10^1$ cells/ml. The seeds were then sown into 700 g of raw, non-sterile soil in plastic tubes. After 10 days or 2 weeks of growth, inoculated plants were harvested, and the bacterial population of the rhizosphere soil, root wash and unsterile root macerate were examined by plating on rif-containing medium (100 μg rif/ml).

FIG. 1 shows bacterial counts (rif-resistant colonies) from portions of the primary root after 10 days of seedling growth. *P. cepacia* 526 was recovered from root tip even when the initial broth inoculum concentration in which the seeds were dipped was as low as 10 bacteria/ml. There was no significant difference in results among inoculum concentrations of $1\times10^5$, $1\times10^3$ and 10 organisms/ml but the $1\times10^7$/ml inoculum treatment showed slightly higher counts. Basal region of the primary root showed higher counts than the mid or root tip region.

FIG. 2 shows recovery of *P. cepacia* 526 (as rif-resistant colonies) from rhizosphere soil, root washings and unsterilized root macerates from 2-week old seedlings after corn seed inoculation. An inoculum level of $1\times10^7$ bacteria per ml showed slightly higher counts than other treatments between which there was no significant difference. Recovery of *P. cepacia* 526 from root washings and unsterile root macerates was higher than from the rhizosphere soil.

To determine the percentage of *P. cepacia* 526 in the total population, root macerates were plated on nutrient agar with and without antibiotics. The inoculant strains accounted for about 99% of the total aerobic heterotroph population of root macerate. No significant difference in colonization was detected when the inoculum was broth or peat based. *P. cepacia* 526 is a good root colonizer, even when applied at low inoculum levels.

EXAMPLE 5

Protection of plants against Fusarium

This example demonstrates the ability of bacterial isolates, showing plate antagonism against Fusarium and good colonization ability to suppress Fusarium fungi infections in plants.

Corn seeds were inoculated using broth culture or peat based inoculum as described in Example 3. The seeds were sown into a 60:40 soil:sand mixture in an aglar's tube (25 mm×200 mm) closed with a rubber stopper at one end. The soil-sand mixture was infected with 10,000 cfu (colony forming units) of *F. moniliforme* per gm of soil by thoroughly mixing in a fungal inoculum prepared as follows: 100 gm of oats in a conical flask were soaked in water overnight. The water was drained off and the flask autoclaved at 121° C. for 15 minutes on 3 successive days. The flask was inoculated with a few pieces of agar culture of *F. moniliforme* and incubated at 28° C. for 2 weeks, shaking daily to keep the grains loose. The grain was later dried and ground in a mill to pass through a 1 mm sieve.

The ability of bacterial isolates to protect corn stems against *F. moniliforme* infection was assessed by determining the extent of invasion of the fungus into the mesocotyl and plumule regions of plants grown from inoculated seed. After 10 days the seed and old roots of the plant were excised and the mesocotyl and plumule regions then were surface sterilized with 4% hypochlorite for 2 minutes. This was followed by 3-4 washings in sterile water. Using a sterile scalpel the plumule region was cut from the mesocotyl region and plated on Wayd antibiotic medium (vide infra) to enumerate Fusarium. Plates were incubated at 25° C. day and 20° C. night temperature with a 12 hour photo period using both fluorescent and "blacklight" illumination. After 3-5 days of incubation, the plates were scored for the presence of chain forming fusaria growing out of the mesocotyl and plumule and the percentage reductions of Fusarium infection determined by comparison to uninoculated controls.

Fungal invasion of the roots was also examined by plating root pieces on Wayd agar medium. Whole roots, after surface sterilization in 4% hypochlorite for 2 minutes, were washed 3-4 times in sterile water and cut using a sterile scalpel into 5 cm pieces. Basal regions, mid regions and root tip regions were plated on Wayd medium.

Figures 5A, 5B:
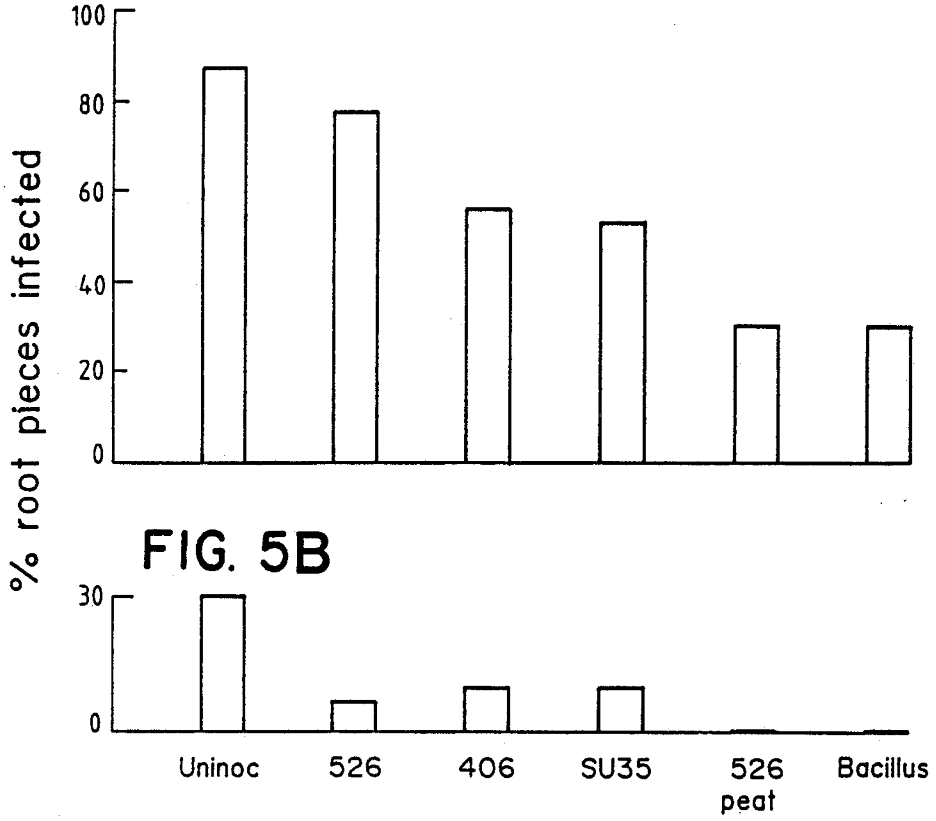
FIG. 5 are graphs showing the reduction of infection of 2 week old corn roots by both total fungi (A) and *F. moniliforme* (B) for various seed inoculants.

Wayd (water agar with yeast and dextrose) medium contained:

Dextrose: 10 g
Yeast extract: 1 g
Agar: 20 g
Water (deionized): 1000 ml
pH 7.0:
filter sterilized antibiotics:
streptomycin sulphate: 1 g
aureomycin: 0.01 g Results from fungal stem and route invasion assays (FIGS. 3-5) showed a significant reduction in *Fusarium moniliforme* infection of mesocotyl, plumule and root following inoculation of seed with *P. cepacia* 526 and 406. Bacillus and Pseudomonas SV35 inoculation also showed a reduction in infection, but to a lesser extent. There was also a reduction in total fungal counts in the mesocotyl and plumule in treatments with strains 526 and 406 (FIG. 4), as well as a significant reduction in total fungal counts on roots in treatments with these strains (FIG. 5).

EXAMPLE 6

Root colonization and protection of plants against Fusarium; Field test

This example demonstrates the response of field grown corn to inoculation with a Fusarium antagonist identified in Example 5, *P. cepacia* 526.

In two field tests near Madison, Wis., the rif-resistant *P. cepacia* strain 526 was used to inoculate seed of 5 inbred parental lines of corn varying in their susceptibility to lodging, and 5 commercial corn hybrids. A broth culture was diluted to make a liquid inoculum which was sprayed in the planting furrow over the seed, at the rate of $10^8$ cells per 2.5 cm row. Corn plants were harvested at 3 weeks after planting. Unsterile root macerates of harvested corn were plated on nutrient agar containing 100 μg/ml rifampicin. *P. cepacia* strain 526 had colonized the root system of the 5 inbred corn seedlings to the extent of $1.7\times10^7$ organisms/g fresh weight of root (mean across all cultivars, see Table 7). This represented 79% of the total population of bacteria on the root capable of growing on nutrient agar. There was little apparent difference between cultivars in their root microbial populations.

A second harvest of corn from treated seeds was taken 77 days after planting. *P. cepacia* strain 526 was still present on the roots of the 5 inbred corn lines as well as the 5 commercial hybrids in inoculated treatments but was not present on uninoculated control plants. When the whole root system was subsampled, population levels of *P. cepacia* 526 were still $10^5$/g fresh weight root, representing 1 to 3% of the total organism population growing on nutrient agar. Inoculation reduced the number of plants lodged from 19 to 9%, mean across 5 cultivars. For the cultivar Co1109, inoculation with *P. cepacia* increased dry matter production of plant tops by 81% from 18.6±3.1 SD to 33.6±8.7 SD g/plant. At a 4 months harvest, cultivar A641 top weight was also increased by inoculation from 86 g fresh weight/plant to 116 g/plant, an increase of 35%. Both of these cultivars are susceptible to lodging. There was little effect of inoculation on the other 3 cultivars in this trial.

TABLE 7

Recovery from Field Grown Corn Roots of the Inoculum Strain 526 of *Pseudomonas cepacia*[1] 3 Weeks after Planting. (organisms/g fresh weight root).

| Cultivar | Total count[2] on nutrient agar | Strain 526 on nutrient agar and rifampicin |
|---|---|---|
| ND246 | $1.4 \times 10^7$ | $1.1 \times 10^7$ |
| A654 | $2 \times 10^7$ | $1.4 \times 10^7$ |
| A554 | $3.7\ 10^7$ | $3.5 \times 10^7$ |
| Co109 | $2.4 \times 10^7$ | $1.7 \times 10^7$ |
| J601 | $1.2 \times 10^7$ | $8 \times 10^6$ |

[1]Inoculated by applying diluted broth culture as a spray over the seed in the furrow at planting.
[2]Values are the means for 4 replicates of unsterile root macerate, harvest 3 weeks after sowing.

EXAMPLE 7

Leaf Colonization by *P. cepacia* 526

Colonization ability of *P. cepacia* 526 was assayed on leaves of tobacco plants in greenhouse experiments. Test inocula were overnight nutrient broth grown cultures of the test organisms. A rifampicin resistant spontaneous mutant of *P. cepacia* was used in this assay. A streptomycin resistant spontaneous mutant of *E. coli* HB101 was also included as a control. Inocula were painted on both sides of leaves using a small paint brush and inoculated leaves were allowed to dry. After 48 hrs, leaf samples were harvested, weighed and 1 g of leaf material was placed in 10 ml of phosphate buffered saline containing 0.1% peptone. Samples were shaken at room temperature for two hours after which appropriate dilutions were plated on nutrient agar with and without antibiotics (100 μg/ml rifampicin or 25 μg/ml streptomycin). Uninoculated control leaves were also assayed for comparison. The natural bacterial flora of the leaf surface (as measured by plating uninoculated leaf samples on NA) are present at the level of $2.5\times10^3$ cell/g leaf. On controls inoculated with *E. coli* HB101, the control strain does not persist after 48 hrs. In contrast, on leaves inoculated with *P. cepacia* 526, the test strain represented 100% of the bacterial population 48 hrs after inoculation.

Leaf colonization was also assessed on cotton plants in the field. Four mature cotton plants were sprayed on both surfaces with rif-resistant *P. cepacia* 526 broth culture containing approximately 10 cfu/ml, using a small fine-spread perfume sprayer.

Leaves were harvested after 8 days, macerated and dilutions (Fahraeus medium) of root macerate were plated on nutrient agar (100 μg/ml rif) and nutrient agar with no antibiotic. Counts of *P. cepacia* 526 recovered on cotton leaves range from about $10^3$ to $10^4$ bacteria/g dry weight leaves. Total bacterial nutrient agar counts ranged from about $10^7$ to $10^8$. *P. cepacia* 526 represents a low percentage of the total population on cotton leaves at 8 days, but did persist on the surface and was recoverable. Field temperatures ranged from 18° C. (night) to 30° C. (day).

Leaf colonization can also be assayed by similar sampling and selective plating experiments using other methods of inoculation including spraying leaves with inoculating compositions of test organisms or inoculating seeds and sampling leaves of plants from these seeds for colonization. *P. cepacia* 526 has been found to colonize leaves of corn, cotton and streptocarpus plants in addition to tobacco.

root macerate samples. These isolates include several related strains represented by strains 526 and 406 from Wisconsin corn samples (Table 8) and strains 64 and 65 isolated from Australian corn samples. A comparison among these isolates and five ATCC cultures designated *P. cepacia* was made. The following *P. cepacia* ATCC strains were included in the comparison: ATCC 25416, species type strain, onion isolate; ATCC 29424, from phthalic acid enrichment; ATCC 17460, from Maraval River, Trinidad; ATCC 10856; and ATCC 17616, from soil enriched with anthraniliate. Two strains identified as *P. cepacia* (Kawamoto and Lorbeer (1976) Plant Disease Reporter 60: 189–191) which are onion isolates and known onion pathogens were also included, strains 64-22NS and 64-22NK. These strains were reported to protect onions from Fusarium infection.

Table 9 summarizes the results of a number of biochemical comparisons among *P. cepacia* strains. No significant distinction can be made among the strains based on the biochemical assays included in Table 9. This supports the identification of these root isolates

TABLE 8

Characterization and comparison of *P. cepacia* root isolates and culture collection strains

| REACTIONS/ENZYMES | 526 | 406 | 64 | 65 | ATCC 29424 | ATCC 17460 | ATCC 25416 | ATCC 10856 | ATCC 17616 | 64-22[1] NS/NK |
|---|---|---|---|---|---|---|---|---|---|---|
| reduction of nitrates of nitrites | + | + | 0 | 0 | + | 0 | 0 | 0 | + | |
| reduction of nitrates to nitrogen | 0 | 0 | 0 | 0 | 0 | + | 0 | 0 | 0 | |
| indole production | 0 | 0 | 0 | 0 | 0 | 0 | 0 | 0 | 0 | |
| acidification with glucose | 0 | 0 | 0 | 0 | 0 | 0 | 0 | 0 | 0 | |
| arginine dihydrolase | 0 | 0 | 0 | 0 | 0 | 0 | 0 | 0 | 0 | |
| urease | 0 | 0 | 0 | 0 | 0 | 0 | 0 | 0 | 0 | |
| hydrolysis (β-glucosidase) | + | + | + | + | 0 | + | + | + | 0 | |
| hydrolysis (protease) + | + | + | + | 0 | + | + | 0 | 0 | | |
| β-galactosidase | + | + | + | + | + | + | + | + | + | |
| glucose assimilation | + | + | + | + | + | + | + | + | + | |
| arabinose assimilation | + | + | + | + | + | + | + | + | + | |
| mannose assimilation | + | + | + | + | + | + | + | + | + | |
| mannitol assimilation | + | + | + | + | + | + | + | + | + | |
| N—acetyl-glucosamine assimilation | + | + | + | + | + | + | + | + | + | |
| maltose assimilation | 0 | 0 | 0 | 0 | 0 | 0 | 0 | 0 | 0 | |
| gluconate assimilation | + | + | + | + | + | + | + | + | + | |
| caprate assimilation | + | + | + | + | + | + | + | + | + | |
| adipate assimilation | + | + | + | + | + | + | + | + | + | |
| malate assimilation | + | + | + | + | + | + | + | + | + | |
| citrate assimilation | + | + | + | + | + | + | + | + | + | |
| phenyl-acetate assimilation | + | + | + | + | + | + | + | + | + | |
| cytochrome oxidase | 0 | 0 | 0 | 0 | 0 | 0 | 0 | + | + | |
| Motility | + | + | + | + | + | + | + | + | + | |
| Gram staining | − | − | − | − | − | − | − | − | − | |
| Pigmentation | yellow | pale yellow | white | white | | | | | | yellow |
| Plate inhibition (in vitro) of:[2] | | | | | | | | | | |
| *Fusarium moniliforme* | 4 | 4 | 4 | 2 | 3 | 5 | 5 | 0 | 0 | 4 |
| Sclerotinia sp. | 4 | 4 | 5 | 2 | 0 | 4 | 1 | 0 | 0 | ND |
| Macrophomina sp. | 3 | 3 | 2 | 1 | 1 | 2 | 2 | 0 | 0 | ND |
| Plant bioassy - % reduction[2] in seedling infection | 62 | 81 | 24 | 0 | 0 | 0 | 4.36 | 5.96 | 33.7 | 0–2.52 |
| Onion pathogenicity test[2] | 1 | 0 | 3 | 3 | 4 | 1 | 3 | 1 | 0 | 4 |
| Corn root colonization[2] at 2 weeks cfu/g dry wt root log 10 units | 6.60 | ND | ND | ND | 6.86 | 6.01 | 5.60 | 6.06 | 6.72 | 6.73–7.10 |

[1]Strains 64-22 NK (Kawamoto and Lorbeer, 1976) were previously typed as *P. cepacia*, and as onion pathogens; these strains were included as positive controls for onion pathogenicity.

[2]Scoring method employed for each property is described in Example 8.

EXAMPLE 8

Characterization of strains of *P. cepacia* type Wisconsin and comparison to *P. cepacia* ATCC cultures Several Fusarium antagonists characterized biochemically as *P. cepacia* have been isolated from unsterilized included as members of the species *P. cepacia*. Several other assays were included in the oomparison: fungal inhibition, onion pathogenicity, corn root colonization and plant protection assays.

Plate inhibition of the fungi *Fusarium moniliforme*, Sclerotinia spp. and Macrophomina spp. were tested by spotting a fresh fungal culture on Potato dextrose agar which had been inoculated 24 hrs. earlier with several spots of a *P. cepacia* culture. After 8–10 more days of incubation at 28° C. (as described above) any fungal free zone around bacterial spots was measured and scored. Inhibition was scored on a scale of 0–5 with 0=no inhibition, 1=1-5 mm of growth inhibition, 2=6–10 mm, 3=11–15 mm, 4=16–20 mm, 5=greater than 21 mm.

Onion pathogenicity (Cother and Dowling (1985) Austral. Plant Pathol. 14: 10–12) was assayed by inoculating white onion tissue with *P. cepacia* cultures. Outer dry scales of onions were peeled and the onions were dipped into 80% alcohol and flamed twice to sterilize the surface. Transverse sections 5 mm thick were then cut from the center of the onion bulb (3–5 pieces/bulb) and placed in a petri dish under sterile conditions with a wet filter paper included to maintain humidity. Plates were then sealed with film and incubated at 30° C. for 72 hrs. Onions were examined at 24, 48 and 72 hrs. Pathogenic reactions were stored on a scale from 0–4, with 0=no reaction, 1=slight yellow discoloration at the site of inoculation, 2=yellow discoloration extending a few mm from the site of inoculation, 3=nearly half of the onion tissue with dark yellow discoloration, 4=entire tissue with brown discoloration.

To test the ability of *P. cepacia* strains to colonize maize seedling roots, seeds were dipped in broth cultures of each strain containing about $10^5$ cell/ml for 10–15 min. Inoculated seeds were then sown in soil tubes (Hawkesbury soil, pH 6.5). After 10–14 days of growth, plants were harvested, and dilutions of unsterile macerate of whole roots were plated on antibiotic selective medium (NA+100 μg/ml rifampicin). Colonization potential of the strains was compared as the rif-resistant TVCC (total viable cell counts)/g dry weight of root.

Suppression of *Fusarium moniliforme* infection by *P. cepacia* strains was determined by measuring the reduction in hypocotyl infection to 10–14 day old corn seedlings grown from inoculated seeds. Corn seeds were inoculated as for colonization assays by dipping in broth cultures. Inoculated seeds and uninoculated controls were then sown in a sand:soil (40:60) mixture infested with ground *Fusarium moniliforme* culture grown on oat seed containing about $10^4$ cfu (colony forming units)/g planting mixture. Stem infection was determined as described in Example 5, by plating excised surface sterilized plant samples on Fusarium growth medium (Wayd Medium). Comparisons were made based on percent reduction of infection compared to uninoculated controls. Results are graphically presented in FIG. 6.

As shown in Table 8, plate inhibition of fungi was variable among the *P. cepacia* strains tested. *P. cepacia* corn root isolates 526, 406 and 64 showed good activity against all three fungi tested. Of the remaining strains tested on all three fungi, only ATCC 14760 had comparable activity. The strains 64-22 NS and 64-22 NK were not tested on all fungi, but did show good activity against Fusarium. *P. cepacia* ATCC 25416 also showed good activity against Fusarium but not against other fungi. ATCC strains 10856 and 17616 showed no antifungal activity in these assays. Further comparisons between ATCC strains and *P. cepacia* root-isolates are given in Table 4.

*P. cepacia* corn root isolates 526 and 406 appear to be non-pathogenic to onions (0 or 1 score, Table 8). In contrast, isolates 64 and 65 are moderate onion pathogens. Again the pathogenicity of ATCC strains toward onions is variable, with ATCC strains 17460, 10856 and 17616 essentially non-pathogenic, while ATCC 25416 and 29424 are moderate and severe pathogens, respectively. The strains 64-22 NK and 64-22 NS, known onion pathogens, scored as severe onion pathogens in this assay.

Colonization potential showed some difference between *P. cepacia* strains; 526, ATCC 29424, ATCC 17616 and the 64-22 NK and NS onion pathogens appear to be better colonizers (root) compared to ATCC strains 17460, 25416 and 10856.

Corn root isolates 526 and 406 are superior at suppressing hypocotyl infection by *Fusarium moniliforme.* Corn root isolate 64 is significantly less effective, while strain 65 displays no protection of corn seedlings in this experiment. Of the ATCC strains only one strain ATCC 17616 shows any significant protection of corn seedlings against fungal infection. It is interesting to note that ATCC 17616 displayed no antifungal activity in plate assays.

Based on the results listed in Table 8, the two strains 526 and 406, which are isolates from corn roots from Wisconsin soils can be clearly differentiated from other *P. cepacia* corn root isolates and from known ATCC strains of *P. cepacia.* These strains and other related isolates listed in Table 1 are herein designated as *P. cepacia* type Wisconsin based on the distinguishing features described above.

EXAMPLE 9

Isolation of *P. cepacia* type Wisconsin

There are several methods for isolating *P. cepacia* type Wisconsin strains from corn root samples or cornfield soil.

Corn root samples are washed, macerated and prepared as in Example 1. Appropriate dilutions of unsterile root macerate are plated on a *Pseudomonas cepacia* selective medium (PC), for example, that described by Burbage et al. (1982) Phytopathology 72: 706. Selections from these platings are purified by streaking on NA. Purified *P. cepacia* corn root isolates are then screened for inhibition of Fusarium as described in Example 2. Root and leaf colonization by the resultant Fusarium antagonist *P. cepacia* selections is confirmed as described in Examples 4 and 7. It is preferred that the biochemical strain characteristics of the resultant presumptive *P. cepacia* type Wisconsin strains be confirmed.

Alternatively, the identity of presumptive *P. cepacia* type Wisconsin strains can be confirmed by agglutination experiments using antisera raised to known *P. cepacia* type Wisconsin strains, the preparation of such antisera is described in Example 10. A sample of presumptive *P. cepacia* type Wisconsin liquid culture (about 10 μl) is added to about 5 μl of a 1:10 dilution of antiserum on a microscope slide. The mixture is allowed to incubate at room temperature for several minutes, after which the mixture is examined under the microscope for agglutination of cells. Samples in which cell agglutination is observed are *P. cepacia* type Wisconsin.

The *P. cepacia* type Wisconsin antisera (like that described in Example 10) can also be used in conventional immunological colony screening (see, for edample, *Methods Enzymol.* (1979) Vol. 68, Wu (ed.), Chapters 30–32, pp. 428–453) to isolate *P. cepacia* type Wisconsin strains. In such a screen, corn root isolates are purified and inoculated onto an appropriate growth medium (i.e., NA). Isolates can be rapidly screened simultaneously by spot inoculating many isolates onto the same growth plate. Plates are incubated to allow bacterial spots to grow up and the spotted isolates are replica plated onto nitrocellulose filters placed over solid growth medium (i.e. NA). Several replicas can then be made and subjected to immunoassay. Alternatively, isolates can be directly spot inoculated onto nitrocellulose filters. Inoculated filters are incubated to allow development of bacterial spots. Inoculated filters are then treated with antiserum, followed by treatment with $^{125}$I-Protein A and autoradiographic detection of *P. cepacia* type Wisconsin strains. Alternate methods of detection of antiserum binding are well known in the art.

*P. cepacia* type Wisconsin strains can be rapidly isolated from corn root samples by combining an initial plating of the corn root samples on *P. cepacia* selective medium followed by immunological screening of the resultant presumptive *P. cepacia* root isolates.

The isolation procedures described above can also be applied to samples of cornfield soil. Soil sample can be directly plated onto *P. cepacia* selective media or an intermediate enrichment step can be employed. Enrichment for root colonizing soil isolates can be done by planting surface sterilized corn seeds in the sample of cornfield soil. Corn plants (10–14 days old) resulting from these seeds are then harvested and unsterile root macerates of these plants are subjected to screening and selection methods described above in order to isolate *P. cepacia* type Wisconsin strains. Root colonizing bacteria are enriched in the plant root and rhizosphere.

EXAMPLE 10

Preparation of *P. cepacia* 526 antiserum

*P. cepacia* 526 was grown overnight in nutrient broth, after which cells were fixed by addition of glutaraldehyde (2% v/v). Cells were killed but not lysed by this procedure. After 2–5 hrs treatment with glutaraldehyde, the cell suspension was dialyzed (72 hrs, 4° C.) against PBS. After dialysis, the cell suspension was adjusted to an optical density (650 nm) of 0.3 to 0.4 by addition of PBS. Cell samples were stored frozen in aliquots. These samples were used as antigen for preparation of *P. cepacia* 526 antiserum.

The following rabbit injection schedule was used in antiserum preparation:

- Day 1 Intravenous injection (IV) of 0.5 ml antigen sample (AG) Subcutaneous injection (SC) of 1.0 ml AG Intramuscular injection (IM) of 0.5 ml AG and 0.5 ml incomplete Freund's adjuvant (IF)
- Day 2 IV 1.0 ml AG
- Day 3 IV 1.5 ml AG
- Day 4–6 Rest
- Day 7 IV 1.5 ml AG
- Day 8 IV 2.0 ml AG
- Day 9 IV 2.0 ml AG
- Day 14 Ear bleeding for titer estimation
- Day 16 SC booster 2.0 ml AG+2.0 ml IF
- Day 21 Cardiac bleeding
- Day 30 SC booster 2.0 ml AG+2.0 ml IF
  - +5 Days Cardiac bleeding
  - +2 Days SC booster 2.0 ml AG without IF
  - +5 Days Cardiac bleeding
  - +2 Days SC booster 2.0 ml AG+2.0 ml IF The last four steps can be repeated as long as desired, alternating boosters with and without Freund's incomplete adjuvant. Rabbits were bled through the marginal ear vein for titer estimation, which was performed by a slide agglutination method. It was found that *P. cepacia* 526 antiserum showed some reaction with *Pseudomonas syringae.* Although *P. cepacia* is readily distinguished from *P. syringae* by conventional criteria, *P. cepacia* 526 antiserum can be subjected to clearing with *P. syringae* antigen prior to use if required. About 10 μl of AG was added to 5 μl of a 1:10 dilution of serum on a microscope slide. The serum was deemed usable if cells clumped to the serum. Comparison was always made to reaction of cells with pre-immune serum. Collected serum of immune rabbits was filtered, sterilized through a 0.45 micron filter, and then frozen at −80° C.

We claim:

1. A method of protecting a plant from disease caused by a fungus comprising inoculating said plant with a strain of *Pseudomonas cepacia* type Wisconsin.

2. The method of claim 1 wherein said inoculation comprises spraying said plant or parts of said plant with an agricultural inoculum which comprises said strain of *Pseudomonas cepacia* type Wisconsin.

3. The method of claim 1 wherein said inoculation comprises applying an agricultural inoculum which comprises said *P. cepacia* type Wisconsin prior to planting.

4. The method of claim 1 wherein said inoculation comprises applying an agricultural inoculum which comprises said strain of *Pseudomonas cepacia* type Wisconsin to soil in which seeds of said plant are planted, said agricultural inoculum being applied in the vicinity of said seeds at the time of planting.

5. The method fo claim 1 wherein said plant is selected from the group consisting of corn, soybean, sorghum, cotton, tobacco, rape, sunflower, pea, tomato or alfalfa.

6. The method of claim 1 wherein said fungus that causes disease is a fungus of the genus Fusarium.

7. The method of claim 6 wherein said plant is corn.

8. The method of claim 1 wherein said *P. cepacia* type Wisconsin is selected from the group of strains consisting of *P. cepacia* 526, 406, 531, 462, or 504.

9. The method of claim 1 wherein said strain of *P. cepacia* type Wisconsin is a mutant or derivative of a strain selected from the group consisting of *P. cepacia* 526, 406, 531, 462, or 504.

10. A bacteria-containing agricultural inoculum suitable for inoculating a plant in the field comprising:

(a) a suitable carrier that is non-phytotoxic, non-bacteriostatic and non-bacteriocidal; and (b) a bacterial strain having the distinguishing characteristics of *Pseudomonas cepacia* type Wisconsin, which strain colonizes leaves or roots of said plant.

11. The inoculum of claim 10 wherein said bacterial strain having the distinguishing characteristics of *Pseudomonas cepacia* type Wisconsin is selected from the group of strains consisting of *P. cepacia* 526, 406, 531, 462, or 504, or mutants or derivatives thereof.

12. A composition of matter comprising a plant seed and a bacterial strain having the distinguishing characteristics of a *Pseudomonas cepacia* type Wisconsin, which strain colonizes a plant or plant parts resulting from germination of said seed.

13. The composition of claim 12 wherein said bacterial strain having the distinguishing characteristics of *P.*

*cepacia* type Wisconsin is selected from the group of strains consisting of *P. cepacia* 526, 406, 531, or 504.

14. The compsoition of claim 12 wherein said bacterial strain having the distinguishing characteristics of *P. cepacia* type Wisconsin is a mutant or derivative of a strain which is selected from the group of strains consisting of *P. cepacia* 526, 406, 531, 462 or 504.

15. The composition of claim 12 wherein said plant seed is seed of a plant selected from the group of plants consisting of corn, sorghum, soybean cotton, rape, sunflower, tobacco, pea, tomato or alfalfa.

16. A substantially purified culture of bacterium having the distinguishing characteristics of a Pseudomonas cepacia type Wisconsin strain, said bacterium having the ability to colonize a part or parts of said plant after inoculation of said plant with said bacterium.

17. The culture of claim 16 wherein said bacterium having the distinguishing characteristics of a *Pseudomonas cepacia* type Wisconsin strain is a strain selected from the group of strains consisting of *P. cepacia* 526, 406, 531, 462, 504 or mutants and derivatives thereof.

18. The culture of claim 16 wherein said plant is selected from the group of plants consisting of corn, sorghum, soybean, rape, tobacco, cotton, sunflower, pea, tomato or alfalfa.

19. A method of isolating a strain of *Pseudomonas cepacia* type Wisconsin which colonizes the roots of plants which comprises the steps:

(a) harvesting roots of plants;

(b) washing said roots of plants to remove soil loosely attached to surfaces of said roots;

(c) macerating said washed roots of plants, thereby preparing root macerate and diluting said root macerate with an appropriate medium;

(c) plating dilutions of said root macerate on an appropriate bacterial growth medium so that bacterial colonies of individual distinct bacterial root isolates can be distinguished;

(e) selecting from said bacterial root isolates those isolates that are *Pseudomonas cepacia* strains;

(f) selecting from said *P. cepacia* root isolates those isolates that are antagonists of a fungus of the genus Fusarium, purifying selected fungal antagonist *P. cepacia* root isolates; and (g) confirming that the selected, purified *P. cepacia* corn root isolates that are antagonistic to a fungus of the genus Fusarium have the distinguishing characteristics of *P. cepacia.*

20. The method of claim 19 wherein said roots of plants are corn roots.

21. The method of claim 19 wherein said plating and selection steps comprise:

(a) plating dilutions of said root macerate on growth medium that is selective for growth of strains of *P. cepacia;* and (b) selecting from said *P. cepacia* root isolates those that are antagonists of a fungus of the genus Fusarium.

22. The method of claim 19 wherein said selection steps comprise immunological screening of said bacterial root isolates for reaction to an antibody raised to a strain of *P. cepacia* type Wisconsin to directly select for root isolates that are strains of *Pseudomonas cepacia* type Wisconsin.

* * * * *

UNITED STATES PATENT AND TRADEMARK OFFICE

CERTIFICATE OF CORRECTION

PATENT NO. : 4,798,723

DATED : Jan. 17, 1989

INVENTOR(S) : Peter J. Dart and K. Prakash Hebber

It is certified that error appears in the above-indentified patent and that said Letters Patent is hereby corrected as shown below:

Column 7, line 3, "Pseudomonas cepacia 526" should read --Pseudomonas cepacia 406--. At column 7, line 4, "Pseudomonas cepacia 406" should read --Peseudomonas cepacia 526--.

Signed and Sealed this

Seventh Day of September, 1993

Attest:

Bruce Lehman

BRUCE LEHMAN

Attesting Officer

Commissioner of Patents and Trademarks